United States Patent [19]
Nichols

[11] Patent Number: 6,087,559
[45] Date of Patent: *Jul. 11, 2000

[54] **PLANT CELLS AND PLANTS TRANSFORMED WITH *STREPTOCOCCUS MUTANS* GENES ENCODING WILD-TYPE OR MUTANT GLUCOSYLTRANSFERASE B ENZYMES**

[75] Inventor: Scott E. Nichols, Johnston, Iowa

[73] Assignee: Pioneer Hi-Bred International, Inc., Des Moines, Iowa

[*] Notice: This patent is subject to a terminal disclaimer.

[21] Appl. No.: 09/007,999

[22] Filed: Jan. 16, 1998

Related U.S. Application Data

[62] Division of application No. 08/478,704, Jun. 7, 1995, abandoned.

[51] Int. Cl.$^7$ .......................... C12N 15/31; C12N 15/54; C12N 15/82; C12N 15/84; C12N 15/89
[52] U.S. Cl. .......................... 800/284; 800/278; 800/287; 800/288; 800/292; 800/293; 800/294; 800/298; 800/317.2; 800/320; 800/320.1; 800/320.2; 800/320.3; 435/69.7; 435/69.8; 435/100; 435/101; 435/193; 435/412; 435/417; 435/419; 435/468; 435/469; 435/470
[58] Field of Search .................................. 800/278, 284, 800/287, 288, 298, 320, 320.1, 320.2, 320.3, 292–294, 317.2; 435/101, 100, 69.1, 193, 320.1, 419, 468, 412, 69.7, 69.8, 417, 469, 470

[56] References Cited

U.S. PATENT DOCUMENTS

| | | | |
|---|---|---|---|
| 4,202,966 | 5/1980 | Misaki et al. | 536/1.11 |
| 4,342,601 | 8/1982 | Yin | 536/123.12 |
| 4,597,830 | 7/1986 | April et al. | 536/123.12 |
| 4,734,162 | 3/1988 | Ampulski | 536/123.12 |
| 5,354,424 | 10/1994 | Rha et al. | 536/123.12 |
| 5,679,880 | 10/1997 | Curtis, III et al. | 800/205 |
| 5,712,107 | 1/1998 | Nichols | 435/278.4 |
| 5,985,666 | 11/1999 | Loiselle et al. | 435/419 |

FOREIGN PATENT DOCUMENTS

| | | |
|---|---|---|
| 06 287 887 | 10/1994 | Japan . |
| 06 313 297 | 11/1994 | Japan . |
| 1122354 | 8/1968 | United Kingdom . |
| WO 95/13389 | 11/1993 | WIPO .......................... C12N 15/82 |
| WO96/06173 | 8/1994 | WIPO .......................... C12N 15/54 |
| WO 96/01904 | 1/1996 | WIPO .......................... C12N 15/82 |
| WO97/29186 | 8/1997 | WIPO . |
| WO94/47808 | 12/1997 | WIPO . |
| WO97/47806 | 12/1997 | WIPO . |

OTHER PUBLICATIONS

Honda, O., et al. "Nucleotide sequence of the *Streptococcus mutans* gtfD gene encoding the glucosyltransferase–S enzyme" J. of General Microbiology (1990)136, 2099–2105.

Napoli et al. "Introduction of a Chimeric Chalcone Synthase Gene into Petunia Results in Reversible Co–Suppression of Homologous Genes *in trans*" The Plant Cell (Apr. 1990) 2, 279–289.

von Schaewen, et al. "Expression of a yeast–derived invertase in the cell wall of tobacco and *Arabidopsis* plants leads to accumulation of carbohydrate and inhibition of photosynthesis and strongly influences growth and phenotype of transgenic tobacco plants" The EMBO Journal (1990) vol. 9 No. 10, pp. 3033–3044.

Kossman, et al. "Transgenic plants as a tool to understand starch biosynthesis" Carbohydrate Bioengineering (1995), Petersen et al., eds., Elsevier Science, pp. 271–278.

Ueda et al. Sequence analysis of the gtfC gene from *Streptococcus mutans* GF–5, Gene. 69 (1988) pp. 101–109.

Hanada, et al. "Isolation and Characterization of the *Streptococcus mutans* gtfC Gene, Coding for Synthesis of Both Soluble and Insoluble Glucans" Infection and Immunity: vol. 56(8) pp. 1999–2005; (1988).

"Mutagenesis" Stratagene Catalog, p. 131.

Hannah, et al. "Maize Methods—Starch Biosynthetic Genes" The Maize Handbook (1994), pp. 624 and 629.

*Primary Examiner*—David T. Fox
*Attorney, Agent, or Firm*—Pioneer Hi–Bred International, Inc.

[57] ABSTRACT

The present invention provides methods of making paper utilizing glucans, produced by glucosyltransferase B enzymes of the species *Streptococcus mutans*, instead of modified starches. The present glucans are functionally similar to the hydroxethyl modified starch and are particularly useful in the sizing and coating steps of paper manufacture. The present glucans also exhibit thermoplastic properties and impart gloss to the paper during the coating step. In particular, the present invention provides plant cells and plants transformed with *Streptococcus mutans* genes encoding wild-type or mutant glucosyltransferase B enzymes.

9 Claims, No Drawings

PLANT CELLS AND PLANTS TRANSFORMED WITH *STREPTOCOCCUS MUTANS* GENES ENCODING WILD-TYPE OR MUTANT GLUCOSYLTRANSFERASE B ENZYMES

This application is a divisional of U.S. patent application Ser. No. 08/478,704, filed Jun. 7, 1995, now abandoned.

FIELD OF THE INVENTION

The present invention involves the field of paper manufacture. Specifically, the present invention provides sources alternative to modified starch in paper manufacture.

BACKGROUND OF THE INVENTION

There are three major phases in paper manufacture where starch is used as an ingredient. The first is the "wet end" where cellulose fibers are mixed with starch in a slurry, and the slurry is forced through a narrow opening onto a wire belt. Water is rapidly removed as the forming sheet travels the length of the belt. After a distance of typically five to fifteen meters on the belt, the sheet has had enough water removed from it so that it can support its own weight. The sheet travels through a number of foils and rolls wherein more water is removed. It is dried to about 11% moisture.

The second phase in paper manufacturing involving starch is the "sizing step". Here, the paper goes through a sizing press where a starch slurry is applied to the sheet. The sheet again goes through a series of foils and rolls. It is dried on rollers and can be taken off the press as a finished product.

The third step involves coating the paper with a mixture of starch and a thermoplastic molecule. On certain lines, this occurs after the sizing step. The nascent roll can also be removed and reinstalled onto a different press for coating. A typical coating device has two blades that run the width of the paper. The blades apply the coating material onto two rolling drums. The paper passes between the drums and the coating material, comprising starch and the thermoplastic moiety, comes off the drums onto the paper. After the paper leaves the drums, it goes through a number of dryers. When the paper is dry, it goes onto a "soft calendar" comprising two drums, one made of a hard density fabric and the other a heated steel drum. The paper passes between the two drums and the heated steel drum is sufficiently hot to melt thermoplastic components of the coating mix providing a hard gloss finish on the paper.

The cellulosic wood pulp fibers, typically used in the above process, are anionic in nature. The addition of a cationic starch to the "wet end" slurry acts as an adhesive by cross linking the pulp fibers through salt linkages. Thus a cross linked polymeric network is made, comprising the starch and cellulose fibers. Typically, the cationic starches used in the "wet end" are tertiary or quaternary amines. These amino groups are added to the starch by wet millers.

Surface sizing starches are used to impart both strength and smooth finish to the sheet after it leaves the "wet end". Such starches also prepare the sheet to receive the various coatings. In cheaper grades of paper and in fiberboard manufacture, sizing starches are used simply as unmodified corn starch. For high grades of paper, chemically-modified starches are used. This is important for the application of a smooth, uniform high quality surface to the paper.

There is a tendency for starches to retrograde i.e. re-form high ordered structures (both helices and crystallites) in an otherwise gelatinous starch slurry. Deposition of retrograded starch onto high quality paper causes regional inconsistencies on the paper and is unacceptable. Furthermore, retrograded starch in the sizing press may necessitate shutting the line down to clear the apparatus.

The starch most often used for sizing applications is a starch having a covalently attached neutral adduct, for instance hydroxyethyl starch. This is prepared by the reaction of ethylene oxide with starch after it is isolated at the wet milling plant. The function of the hydroxyethyl (or similar) adduct is independent of its chemical nature; rather, it serves to provide steric hindrance, inhibiting the formation of high ordered structures. This steric hindrance is critical to decrease retrogradation. The periodic protuberance afforded by the adduct disrupts the formation of higher ordered structures that leads to retrogradation.

Speed is of paramount importance in paper manufacturing. Limiting in press speed is starch consistency. Presses often run below their full capacity speeds. Depending on the application, starch slurries are between 3–15% (usually 5–6%) solids. An increase in solids would necessarily result in a decrease in the amount of water that would have to be removed from a paper sheet being manufactured. This would allow the press to work at higher speeds.

Hydroxethylated starch also forms higher ordered structures as the temperature decreases or the concentration increases. The formation of the higher ordered structures on the surface of the paper is required. After application to the sheet the starch reforms some of these higher ordered structures and creates a uniform surface that imparts structural strength and facilitates the acceptance of inks and dyes. However, the higher ordered structures should not form in the slurry nor on the application device because this necessitates shutting down the production line to clear off retrograded starch.

The function of the hydroxyethyl group is to lower the temperature and/or raise the concentration of starch at which retrogradation occurs. As the processing lines have already been optimized for a particular temperature of the starch slurry, a decrease in the tendency to retrograde would allow for a higher carbohydrate content in the slurry.

The mixture applied to the paper sheet in the coating process contains hydroxethylated starch and thermoplastic molecules. The most prevalent thermoplastic molecules used are latexes, such as styrene butadiene. The function of the hydroxethyl starch is as indicated above. The function of the thermoplastic molecule is to form a high gloss finish on the paper. This causes an increased ability to take inks and dyes and improves the resolution, in general, on the printed sheet.

Based on the foregoing, there exists a need, in paper manufacturing, for modified starch substitutes which are functionally similar to modified starch. There is a further need to provide substitutes for modified starch which are less prone to retrogradation. There is a further need to provide methods of manufacturing paper which are faster than current methods and allow presses to run closer to their full capacity speed. There is a further need to provide methods of manufacturing paper that are environmentally-friendly and do not involve input materials that require chemical processing.

It is therefore an object of the present invention to provide substitutes for modified starch which are less prone to retrogradation when used in paper manufacture.

It is a further object of the present invention to provide methods of manufacturing paper which are faster and more efficient than existing methods.

It is a further object of the present invention to provide substitutes for starch in paper manufacturing that do not require costly chemical modification as does starch.

It is a further object of the present invention to provide methods for manufacturing paper that are more environmentally-friendly than existing methods.

It is a further object of the present invention to provide substitutes for thermoplastic molecules currently used in the coating step during paper manufacture.

SUMMARY OF THE INVENTION

The present invention provides glucans which can be used as substitutes for a modified starch and/or latex in paper manufacturing. The present glucans are produced by glucosyltransferase B ("GTF B") enzymes of the species *Streptococcus mutans*, and are functionally similar to the modified starch currently used in paper manufacturing. The present glucans also exhibit similar physical properties to the thermoplastic molecules currently used in the coating step of paper manufacturing.

The present invention also provides methods of manufacturing paper utilizing the present glucans, input materials that are produced biologically. Thus, the present methods are more cost-effective and environmentally-friendly than current methods which require input materials producing chemical effluents.

DETAILED DESCRIPTION OF THE INVENTION

Sequences
  Seq ID No. 1-the gtfb, cDNA sequence
  Seq ID No. 2-the GTFB protein sequence encoded by Seq ID No. 1

As used herein, "glucan" means a glucose polymer having linkages that are α(1→3), α(1→6), and branching α(1→3, 6).

As used herein, "amyloplast" means starch accumulating organelle in plant storage tissue.

As used herein, "vacuole" means the cellular compartment bounded by the tonoplast membrane.

*Streptococcus mutans* is a species that is endogenous to the oral cavity and colonizes tooth enamel. See e.g. Kuramitsu, "Characterization of Extracellular Glucosyl Transferase Activity of *Streptococcus mutans*." *Infect. Immun.*; Vol. 12(4); pp.738–749; (1975); and Yamashita, et al., "Role of the *Streptococcus mutans* gtf Genes in Caries Induction in the Specific-Pathogen-Free Rat Model," *Infect. Immun.*; Vol. 61(9); pp. 3811–3817; (1993); both incorporated herein their entirety by reference. *Streptococcus mutans* species secrete glucosyltransferase B ("GTF B") enzymes which utilize dietary sucrose to make a variety of extracellular glucans. See e.g. Kametaka, et al., "Purification and Characterization of Glucosyltransferase from *Streptococcus mutans* OMZ 176 with Chromatofocusing," *Microbios*; Vol. 51(206); pp. 29–36; (1978); incorporation herein by reference.

Both soluble and insoluble glucans are synthesized, and the proteins responsible have been isolated and characterized. See e.g. Aoki, et al., "Cloning of a *Streptococcus mutans* Glucosyltransferase Gene Coding for Insoluble Glucan Synthesis," *Infect. Immun.*; Vol. 53(3); pp. 587–594; (1986); Shimamura, et al., "Identification of Amino Acid Residues in *Streptococcus mutans* Glucosyltransferases Influencing the Structure of the Glucan Produced," *J. Bacteriol.*; Vol. 176(16); pp. 4845–50; (1994); and Kametaka, et al., "Purification and Characterization of Glucosyltransferase from *Streptococcus mutans* OMZ176 with Chromatofocusing," *Microbios*; Vol. 51(206); pp. 29–36; (1987); all incorporated herein their entirety by reference.

The proteins involved are large (~155 kDa) and catalyze the group transfer of the glucosyl portion of sucrose to an acceptor glucan via (1→3) and (1→6) linkages. See e.g., Wenham, et al., "Regulation of Glucosyl Transferase and Fructosyl Transferase Synthesis by Continuous Cultures of *Streptococcus mutans*," *J. Gen. Microbiol.*; Vol. 114 (Part 1); pp. 117–124; (1979); Fu, et al., "Maltodextrin Acceptor Reactions of *Streptococcus mutans* 6715 glucosyltransferases," *Carbohydr. Res.*; Vol. 217; pp. 210–211; (1991); and Bhattacharjee, et al., "Formation of Alpha—(1→6), Alpha—(1→3), and Alpha (1→2) Glycosidic Linkages by Dextransucrase from *Streptococcus Sanguis* in Acceptor-Dependent Reactions," *Carbohydr. Res.*; Vol. 242; pp. 191–201; (1993); all incorporated herein their entirety by reference.

The genes involved in glucan synthesis have been isolated and sequenced. See Shimamura, et al., cited hereinabove and Russel, et al., "Expression of a Gene for Glucan-binding Protein from *Streptococcus-mutans* in *Escherichia-coli*," *J. Gen. Microbiol.*; Vol. 131(2); pp. 295–300; (1985); Russell et al., "Characterization of Gilucosyltransferase Expressed from a *Streptococcus-Sobrinus* gene cloned in *Escherichia-coli*," *J. Gen. Microbiol.*; Vol. 133(4); pp. 935–944; (1987); and Shiroza, et al., "Sequence Analysis of the gtfb Gene from *Streptococcus mutans*," *J. Bacteriol.*; Vol. 169(9); pp. 4263–4270; (1987); all incorporated herein in their entirety by reference.

The structures of the various glucans produced by GTF enzymes are quite heterogeneous with respect to the proportions of (1→3), (1→6) and (1→3,6) branches present in any given glucan. Transformation of genes which encode naturally occurring GTF B and GTF B mutant proteins into plants, such as maize, provides amyloplasts and vacuoles with novel compositions.

GTF B enzyme activity incorporated into the amyloplast and/or vacuole leads to the accumulation of starch and glucan in the same amyloplast and/or vacuole. Retrogradation occurs as portions of starch molecules interact and subsequently form inter- or intra-chain helices. In a mixture of starch and glucans, the frequency of starch-starch interactions, that lead to helix formation, is diminished. A paste made from the mixed polymers is less prone to retrogradation as a result. This is especially true in the starch accumulation mutants envisioned as transformation targets where the relative proportion of starch is reduced.

Glucans produced in maize amyloplasts and/or vacuoles by the transgenic GTF B enzymes can function in paper processing without chemical modification, as required of starch. The polymer solution consequently has altered rheological properties and is less prone to retrogradation compared to starch. The glucans are branched and irregular and able to supplant modified starches with comparable or superior efficacy. They do not require any costly chemical modification as does starch. For coating applications, the present glucans exhibit thermoplastic properties in addition to the above advantages.

The wild type GTF and mutants thereof useful in producing glucans according to the present invention are provided below. The following code is employed:

| Amino Acid | One-letter Symbol |
| --- | --- |
| Alanine | A |
| Asparagine | N |
| Aspartic Acid | D |
| Glutamine | Q |
| Glutamic Acid | E |
| Isoleucine | I |
| Lysine | K |
| Threonine | T |
| Tyrosine | Y |
| Valine | V |

The nomenclature used to identify the mutant GTF B enzymes used to produce the present glucans is as follows: the number refers to the amino acid position in the polypeptide chain; the first letter refers to the amino acid in the wild type enzyme; the second letter refers to the amino acid in the mutated enzyme; and enzymes with multiple mutations have each mutation separated by /.

The mutant GTF B enzyme used to produce glucans for paper coating is preferably selected from the group consisting of I448V; D457N; D567T; K1014T; D457N/D567T;

| D457N/D571K; | D567T/D571K; | D567T/D571K/K1014T; |
| --- | --- | --- |

I448V/D457N/D567T/D571K/K779Q/K1014T; and Y169A/Y170A/Y171A.

The mutant GTF B enzyme used to produce glucans for paper coating is more preferably selected from the group consisting of I448V; K1014T;D567T/D571K/K1014T; I448V/D457N/D567T/D571K/K779Q/K1014T; and Y169A/Y170A/Y171A.

The mutant GTF B enzyme used to produce glucans for paper coating is even more preferably selected from the group consisting of K1014T; I448V/D457N/D567T/D571K/K779Q/K1014T; and Y169A/Y170A/YI71A.

The mutant GTF B enzyme used to produce glucans for paper coating is most preferably I448V/D457N/D567T/D571K/K779Q/K1014T; or Y169A/Y170A/Y171A.

The mutant GTF B enzyme used to produce glucans for paper sizing is preferably selected from the group consisting of I448V; D457N; D567T; K779Q; K1014T; D457N/D567T; D457N/D571K; D567T/D571K and D567T/D571K/K1014T.

The mutant GTF B enzyme used to produce glucans for paper sizing is more preferably selected from the group consisting of I448V; D457N: K779Q; D567T/D571K; and D567T/D571K/K1014T.

The mutant GTF B enzyme used to produce glucans for paper sizing is most preferably I448V.

The glucans of the present invention are preferably produced in transgenic maize, potato, cassava, sweet potato, rye, barley, wheat, sorghum, oats, millet, triticale, sugarcane or rice. More preferably, the present glucans are produced in maize, potato, sugarcane, cassava or sweet potato. Even more preferably, the present glucans are produced in maize or potato. Most preferably, the present glucans are produced in maize.

In a highly preferred embodiment of the present invention, maize lines deficient in starch biosynthesis are transformed with mutant GTF B genes. Such lines may be naturally occurring maize mutants (i.e. $sh_2$, $bt_2$, $bt_1$) or transgenic maize engineered so as to accumulate low amounts of starch in the endosperm when compared to wild type maize. See e.g. Müller-Röber, et al. "Inhibition of the ADP-glucose Pyrophosphorylase in Transgenic Potatoes Leads to Sugar-Storing Tubers and Influences Tuber Formation and Expression of Tuber Storage Protein Genes," *The EMBO Journal*; Vol. 11(4); pp. 1229–1238; (1992); and Creech, "Carbohydrate Synthesis in Maize," *Advances in Agronomy*; Vol. 20; pp. 275–322; (1968); both incorporated herein in their entirety by reference.

The production of the present glucans is performed according to methods of transformation that are well known in the art, and thus constitute no part of this invention. The compounds of the present invention are synthesized by insertion of an expression cassette containing a synthetic gene which, when transcribed and translated, yields a GTF enzyme that produces the desired glucan. Such empty expression cassettes, providing appropriate regulatory sequences for plant expression of the desired sequence, are also well-known, and the nucleotide sequence for the synthetic gene, either RNA or DNA, can readily be derived from the amino acid sequence for the protein using standard texts and the references provided. The above-mentioned synthetic genes preferably employ plant-preferred codons to enhance expression of the desired protein.

The following description further exemplifies the compositions of this invention and the methods of making and using them. However, it will be understood that other methods, known by those of ordinary skill in the art to be equivalent, can also be employed.

The genes which code for the present enzyme or mutants can be inserted into an appropriate expression cassette and introduced into cells of a plant species. Thus, an especially preferred embodiment of this method involves inserting into the genome of the plant a DNA sequence coding for a mutant or wild type gene in proper reading frame, together with transcription promoter and initiator sequences active in the plant. Transcription and translation of the DNA sequence under control of the regulatory sequences causes expression of the protein sequence at levels which provide an elevated amount of the protein in the tissues of the plant.

Synthetic DNA sequences can then be prepared which code for the appropriate sequence of amino acids of a GTF B protein, and this synthetic DNA sequence can be inserted into an appropriate plant expression cassette.

Likewise, numerous plant expression cassettes and vectors are well known in the art. By the term "expression cassette" is meant a complete set of control sequences including promoter, initiation, and termination sequences which function in a plant cell when they flank a structural gene in the proper reading frame. Expression cassettes frequently and preferably contain an assortment of restriction sites suitable for cleavage and insertion of any desired structural gene. It is important that the cloned gene have a start codon in the correct reading frame for the structural sequence.

By the term "vector" herein is meant a DNA sequence which is able to replicate and express a foreign gene in a host cell. Typically, the vector has one or more restriction endonuclease recognition sites which may be cut in a predictable fashion by use of the appropriate enzyme such vectors are preferably constructed to include additional structural gene sequences imparting antibiotic or herbicide resistance, which then serve as markers to identify and separate transformed cells. Preferred markers/selection agents include kanamycin, chlorosulfuron, phosphonothricin, hygromycin and methotrexate. A cell in which the foreign genetic material in a vector is functionally expressed has been "transformed" by the vector and is referred to as a "transformant".

A particularly preferred vector is a plasmid, by which is meant a circular double-stranded DNA molecule which is not a part of the chromosomes of the cell.

As mentioned above, both genomic DNA and cDNA encoding the gene of interest may be used in this invention. The gene of interest may also be constructed partially from a cDNA clone and partially from a genomic clone. When the gene of interest has been isolated, genetic constructs are made which contain the necessary regulatory sequences to provide for efficient expression of the gene in the host cell. According to this invention, the genetic construct will contain (a) a genetic sequence coding for the protein or trait of interest and (b) one or more regulatory sequences operably linked on either side of the structural gene of interest. Typically, the regulatory sequences will be selected from the group comprising of promoters and terminators. The regulatory sequences may be from autologous or heterologous sources.

The expression cassette comprising the structural gene for a mutant of this invention operably linked to the desired control sequences can be ligated into a suitable cloning vector. In general, plasmid or viral (bacteriophage) vectors containing replication and control sequences derived from species compatible with the host cell are used. The cloning vector will typically carry a replication origin, as well as specific genes that are capable of providing phenotypic selection markers in transformed host cells. Typically, genes conferring resistance to antibiotics or selected herbicides are used. After the genetic material is introduced into the target cells, successfully transformed cells and/or colonies of cells can be isolated by selection on the basis of these markers.

Typically, an intermediate host cell will be used in the practice of this invention to increase the copy number of the cloning vector. With an increased copy number, the vector containing the gene of interest can be isolated in significant quantities for introduction into the desired plant cells. Host cells that can be used in the practice of this invention include prokaryotes, including bacterial hosts such as *E. coli S. typhimurium*, and *Serratia marcescens*. Eukaryotic hosts such as yeast or filamentous fungi may also be used in this invention. Since these hosts are also microorganisms, it will be essential to ensure that plant promoters which do not cause expression of the protein in bacteria are used in the vector.

The isolated cloning vector will then be introduced into the plant cell using any convenient technique, including electroporation (in protoplasts), retroviruses, bombardment, and microinjection into cells from monocotyledonous or dicotyledonous plants in cell or tissue culture to provide transformed plant cells containing as foreign DNA at least one copy of the DNA sequence of the plant expression cassette. Using known techniques, protoplasts can be regenerated and cell or tissue culture can be regenerated to form whole fertile plants which carry and express the gene for a protein according to this invention. Accordingly, a highly preferred embodiment of the present invention is a transformed maize plant, the cells of which contain as foreign DNA at least one copy of the DNA sequence of an expression cassette of a GTF B mutant.

It will also be appreciated by those of ordinary skill that the plant vectors provided herein can be incorporated into *Agrobacterium tumefaciens*, which can then be used to transfer the vector into susceptible plant cells, primarily from dicotyledonous species. Thus, this invention provides a method for introducing GTF B in *Agrobacterium tumefaciens*-susceptible dicotyledonous plants in which the expression cassette is introduced into the cells by infecting the cells with *Agrobacterium tumefaciens*, a plasmid of which has been modified to include a plant expression cassette of this invention.

For example, the potato plant can be transformed via *Agrobacterium tumefaciens* to produce the present glucans. The transformation cassette comprises a patatin promoter, followed by the relevant gtfb coding sequence and the neomycin phosphotransferase polyadenylation site/terminator. See e.g. Utsumi, et al., "Expression and Accumulation for Normal and Modified Soybean Glycinins in Potato Tubers," *Plant Science*; Vol. 102(2); pp. 181–188; (1994); (Limerick); incorporated herein in its entirety by reference. The transgenic cassette is placed into a transformation vector. For example, BIN19, or lo derivatives thereof, are useful when transforming via *Agrobacterium tumefaciens*. See e.g. Visser, et al., "Transformation of Homozygous Diploid Potato with an *Agrobacterium tumefaciens* Binary Vector System by Adventitious Shoot Regeneration on Leaf and Stem Segments," *Plant Mol. Biol.*; Vol. 12(3); pp. 329–338; (1989); incorporated herein in its entirety by reference.

For maize transformation vectors, the promoters include any promoter whose expression is specific and limited to endosperm cells. Included are those encoding either 22 kDa zein, opaque2, gamma zein and waxy. These lead into the gtfb gene and are followed by the endogenous terminator or the heterogeneous PINII terminator. The GTF B protein are directed to the maize endosperm amyloplast using a suitable transit sequence.

Transit sequences useful in directing the enzyme into the amyloplast for accumulation within the amyloplast include but are not limited to ribulose biophosphate carboxylase small subunit, waxy, brittle-l, and chlorophyll AB binding protein. The transit sequences are juxtaposed between the promoter and the GTF B coding sequence and fused in translational reading frame with the GTF B moiety.

Transit sequences useful in directing the enzyme into the vacuole for accumulation within the vacuole are well known in the art. For vacuolar targeting, see e.g. Ebskamp, et al., "Accumulation of Fructose Polymers in Transgenic Tobacco," *Bio/technology*; Vol. 12; pp. 272–275; (1994); incorporated herein in its entirety by reference.

For maize transformation and regeneration see e.g. Armstrong, C., "Regeneration of Plants from Somatic Cell Cultures: Applications for in vitio Genetic M4anipulation," *The Maize Handbook*; Freeling, et al., eds, pp. 663–671; (1994); incorporated herein in its entirety by reference.

Once a given plant is transformed, the glucans synthesized can be isolated, by standard methods, known to one skilled in the art. The glucan thus obtained in the transgenic plant can be substituted for modified starches and utilized in the sizing and/or coating steps. For formulations useful in the coating step, see e.g. Heiser, et al., "Starch Formations," *Starch and Starch Products in Paper Coating*; Kearney, et al., eds., pp. 147–162; (1990); Tappi Press; incorporated herein in its entirety by reference.

In both sizing and coating, the present glucans are utilized in an amount of from about 4 to about 15 weight percent, more preferably from about 5 to about 12 weight percent, also preferably from about 6 to about 8 weight percent. Weight percent is defined as grams of molecule per 100 ml solution.

The present glucans are used to replace the starch and/or latex molecules completely, or a starch-glucan or a latex-glucan mixture is used in the slurry. In the sizing application, the glucan:starch ratio ranges from about 10:90 to about 100:0; more preferably from about 40:60 to about 100:0;

more preferably still from about 60:40 to about 100:0; most preferably about 100:0.

In the coating application, the glucan:starch ratio ranges from about 10:90 to about 100:0; more preferably from about 40:60 to about 100:0; more preferably still from about 60:40 to about 100:0; most preferably about 100:0. In the coating application, the glucan:latex ratio ranges from about 10:90 to about 100:0; more preferably from about 40:60 to about 100:0; more preferably still from about 60:40 to about 100:0; most preferably about 100:0.

All publications cited in this application are indicative of the level of skill of those skilled in the art to which this invention pertains. All publications are herein incorporated by reference to the same extent as if each individual publication or patent application was specifically and individually indicated to be incorporated by reference.

Variations on the above embodiments are within the ability of one of ordinary skill in the art, and such variations do not depart from the scope of the present invention as described in the following claims.

What claimed is:

1. A transgenic plant cell containing a DNA molecule, encoding a transit sequence and a *Streptococcus mutans* glucosyltransferase B enzyme, wild type or mutant, wherein the mutant is I448V; D457N; D567T; K1014T; D457N/D567T; D457N/D571K; D567T/D571K; D567T/D571K/K1014T; I448V/D457N/D567T/D571K/K779Q/K1014T; or Y169A/Y170A/Y171A, wherein the transit sequence directs the enzyme to the amyloplast or vacuole and wherein the plant cell is derived from a plant selected from the group consisting of potato, cassava, sweet potato and sugar cane.

2. The plant cell of claim 1 which is transformed by *Agrobacteriuim tumefaciens*, electroporation, retroviruses, bombardment or microinjection.

3. A transgenic plant regenerated from the plant cell of claim 1.

4. A maize line deficient in starch biosynthesis containing a DNA molecule, encoding a transit sequence and a *Streptococcus mutans* glucosyltransferase B enzyme, wild type or mutant, wherein the mutant is I448V; D457N; D567T; K1014T; D457N/D567T; D457N/D571K; D567T/D571K; D567T/D571K/K1014T; I448V/D457N/D567T/D571K/K779Q/K/K1014T; or Y169A/Y170A/Y 171A, wherein the transit sequence directs the enzyme to the amyloplast or vacuole.

5. The plant of claim 4 wherein the plant is maize of genotype $sh_2$, $bt_2$ or $bt_1$.

6. A transgenic plant seed containing a DNA molecule, encoding a transit sequence and a *Streptococcus mutans* glucosyltransferase B enzyme, wild type or mutant, wherein the mutant is I448V; D457N; D567T; K1014T; D457N/D567T; D457N/D571K; D567T/D571K; D567T/D571K/K1014T; I448V/D457N/D567T/D571K/ K779Q/K1014T; or Y169A/Y170A/Y171A, wherein the transit sequence directs the enzyme to the amyloplast or vacuole and wherein the plant seed is derived from a plant selected from the group consisting of maize, rye, barley, wheat, sorghum, oats, millet, triticale and rice.

7. The plant seed of 6 wherein the enzyme produces an insoluble product.

8. The plant seed of claim 6 wherein the enzyme is a mutant of glucosyltransferase B selected from the group consisting of I448V; D457N; D567T; K1014T; D457N/D567T; D457N/D571K; D567T/D571K; D567T/D571K/K1014T; I448V/D457N/D567T/D571K/K779Q/K1014T; and Y169A/Y170A/Y171A.

9. The plant seed of claim 6 wherein the DNA molecule contains a promoter selected from the group consisting of 22 kDa zein, opaque2, gamma zein and waxy gene promoters.

* * * * *

SEQUENCE LISTING

<160> NUMBER OF SEQ ID NOS: 2

<210> SEQ ID NO 1
<211> LENGTH: 4460
<212> TYPE: DNA
<213> ORGANISM: Streptococcus mutans
<220> FEATURE:
<221> NAME/KEY: CDS
<222> LOCATION: (9)...(4434)

<400> SEQUENCE: 1

```
ggttccta atg gac aag aaa gtg cgt tat aaa ctg cgc aaa gtt aaa aaa        50
         Met Asp Lys Lys Val Arg Tyr Lys Leu Arg Lys Val Lys Lys
          1               5                   10 aga tgg gtg aca gta tct gtt gca tct gct gtg atg act tta act aca        98
Arg Trp Val Thr Val Ser Val Ala Ser Ala Val Met Thr Leu Thr Thr
 15                  20                  25                  30 ctt tcg ggt ggc ttg gtt aaa gca gat tct aat gaa tcg aaa tcc caa       146
Leu Ser Gly Gly Leu Val Lys Ala Asp Ser Asn Glu Ser Lys Ser Gln
                 35                  40                  45 att tct aat gat tct aat acc agt gtt gtt act gct aat gaa gaa tct       194
Ile Ser Asn Asp Ser Asn Thr Ser Val Val Thr Ala Asn Glu Glu Ser
             50                  55                  60 aat gta ata acc gaa gcg aca tct aag caa gaa gct gct agt agt caa       242
Asn Val Ile Thr Glu Ala Thr Ser Lys Gln Glu Ala Ala Ser Ser Gln
         65                  70                  75 act aat cat aca gta acg aca agc agt agc tct act tcg gta gtt aat       290
Thr Asn His Thr Val Thr Thr Ser Ser Ser Ser Thr Ser Val Val Asn
 80                  85                  90 ccc aaa gag gtt gta agt aat cct tat act gtt ggg gaa aca gct tct       338
Pro Lys Glu Val Val Ser Asn Pro Tyr Thr Val Gly Glu Thr Ala Ser
 95                 100                 105                 110 aat ggt gaa aag ctt caa aat caa aca act aca gtt gac aaa act tct       386
Asn Gly Glu Lys Leu Gln Asn Gln Thr Thr Thr Val Asp Lys Thr Ser
                115                 120                 125 gaa gct gct gct aat aat att agt aaa caa aca acc gaa gct gat aca       434
Glu Ala Ala Ala Asn Asn Ile Ser Lys Gln Thr Thr Glu Ala Asp Thr
            130                 135                 140 gat gtt att gat gat agc aat gca gcc aat cta caa ata ttg gaa aaa       482
Asp Val Ile Asp Asp Ser Asn Ala Ala Asn Leu Gln Ile Leu Glu Lys
        145                 150                 155 ctt ccc aat gta aaa gaa att gat ggt aag tat tat tat gac aat        530
Leu Pro Asn Val Lys Glu Ile Asp Gly Lys Tyr Tyr Tyr Tyr Asp Asn
    160                 165                 170 aac ggc aaa gtt cgt act aat ttt aca tta att gct gat ggc aaa att       578
Asn Gly Lys Val Arg Thr Asn Phe Thr Leu Ile Ala Asp Gly Lys Ile
175                 180                 185                 190 tta cat ttt gat gaa act ggc gct tat act gat aca tca att gac act       626
Leu His Phe Asp Glu Thr Gly Ala Tyr Thr Asp Thr Ser Ile Asp Thr
```

```
                        195                 200                 205
gta aat aaa gat atc gtc aca aca aga agt aat cta tac aaa aaa tat     674
Val Asn Lys Asp Ile Val Thr Thr Arg Ser Asn Leu Tyr Lys Lys Tyr
                210                 215                 220 aat caa gtt tat gat cgc tct gca cag agc ttt gag cat gtt gat cat     722
Asn Gln Val Tyr Asp Arg Ser Ala Gln Ser Phe Glu His Val Asp His
            225                 230                 235 tat ttg aca gct gag agt tgg tat cgt cct aag tac atc ttg aag gat     770
Tyr Leu Thr Ala Glu Ser Trp Tyr Arg Pro Lys Tyr Ile Leu Lys Asp
        240                 245                 250 ggc aaa aca tgg aca cag tca aca gaa aaa gat ttc cgt ccc tta ttg     818
Gly Lys Thr Trp Thr Gln Ser Thr Glu Lys Asp Phe Arg Pro Leu Leu
255                 260                 265                 270 atg aca tgg tgg cct gac caa gaa acg cag cgt caa tat gtt aac tac     866
Met Thr Trp Trp Pro Asp Gln Glu Thr Gln Arg Gln Tyr Val Asn Tyr
                275                 280                 285 atg aat gca cag ctt ggc att aac aag act tat gat gat aca agt aat     914
Met Asn Ala Gln Leu Gly Ile Asn Lys Thr Tyr Asp Asp Thr Ser Asn
            290                 295                 300 caa ttg caa tta aat att gca gct gca act att caa gca aaa att gag     962
Gln Leu Gln Leu Asn Ile Ala Ala Ala Thr Ile Gln Ala Lys Ile Glu
        305                 310                 315 gcc aaa att aca act tta aag aat act gat tgg ctg cgt cag act att    1010
Ala Lys Ile Thr Thr Leu Lys Asn Thr Asp Trp Leu Arg Gln Thr Ile
320                 325                 330 tcc gca ttt gtt aag aca cag tca gct tgg aac agt gac agc gaa aaa    1058
Ser Ala Phe Val Lys Thr Gln Ser Ala Trp Asn Ser Asp Ser Glu Lys
335                 340                 345                 350 ccg ttt gat gat cat tta caa aat gga gca gtg ctt tac gat aat gaa    1106
Pro Phe Asp Asp His Leu Gln Asn Gly Ala Val Leu Tyr Asp Asn Glu
                355                 360                 365 gga aaa tta acg cct tat gct aat tcc aac tac cgt atc tta aat cgc    1154
Gly Lys Leu Thr Pro Tyr Ala Asn Ser Asn Tyr Arg Ile Leu Asn Arg
            370                 375                 380 acc ccg acc aat caa acc gga aag aaa gat cca agg tat aca gct gat    1202
Thr Pro Thr Asn Gln Thr Gly Lys Lys Asp Pro Arg Tyr Thr Ala Asp
        385                 390                 395 aac act atc ggc ggt tat gaa ttc ctt ttg gcc aac gat gtg gat aat    1250
Asn Thr Ile Gly Gly Tyr Glu Phe Leu Leu Ala Asn Asp Val Asp Asn
    400                 405                 410 tct aat cct gtc gtg cag gcc gaa caa ttg aac tgg cta cat ttt ctc    1298
Ser Asn Pro Val Val Gln Ala Glu Gln Leu Asn Trp Leu His Phe Leu
415                 420                 425                 430 atg aac ttt ggt aac att tat gcc aat gat ccg gat gct aac ttt gat    1346
Met Asn Phe Gly Asn Ile Tyr Ala Asn Asp Pro Asp Ala Asn Phe Asp
                435                 440                 445 tcc att cgt gtt gat gcg gta gat aat gtg gat gct gac ttg ctc caa    1394
Ser Ile Arg Val Asp Ala Val Asp Asn Val Asp Ala Asp Leu Leu Gln
            450                 455                 460 att gct ggg gat tac ctc aaa gct gct aag ggg atc cat aaa aat gat    1442
Ile Ala Gly Asp Tyr Leu Lys Ala Ala Lys Gly Ile His Lys Asn Asp
        465                 470                 475 aag gct gct aat gat cat ttg tct att tta gag gca tgg agt gac aac    1490
Lys Ala Ala Asn Asp His Leu Ser Ile Leu Glu Ala Trp Ser Asp Asn
    480                 485                 490 gac act cct tac ctt cat gat gat ggc gac aat atg att aat atg gac    1538
Asp Thr Pro Tyr Leu His Asp Asp Gly Asp Asn Met Ile Asn Met Asp
495                 500                 505                 510 aat aag ctg cgt ttg tct cta tta ttt tca tta gct aaa ccc tta aat    1586
```

```
            Asn Lys Leu Arg Leu Ser Leu Leu Phe Ser Leu Ala Lys Pro Leu Asn
                            515                 520                 525 caa cgt tca ggc atg aat cct ctg atc act aac agt ttg gtg aat cgt        1634
Gln Arg Ser Gly Met Asn Pro Leu Ile Thr Asn Ser Leu Val Asn Arg
            530                 535                 540 act gat gat aat gct gaa act gcc gca gtc cct tct tat tcc ttc atc        1682
Thr Asp Asp Asn Ala Glu Thr Ala Ala Val Pro Ser Tyr Ser Phe Ile
            545                 550                 555 cgt gcc cat gac agt gaa gtg cag gat ttg att gct gat atc atc aag        1730
Arg Ala His Asp Ser Glu Val Gln Asp Leu Ile Ala Asp Ile Ile Lys
            560                 565                 570 gca gaa atc aat cct aat gtt gtc ggg tat tca ttc act atg gag gaa        1778
Ala Glu Ile Asn Pro Asn Val Val Gly Tyr Ser Phe Thr Met Glu Glu
575                 580                 585                 590 atc aag aag gct ttc gag att tac aac aaa gac tta tta gct aca gag        1826
Ile Lys Lys Ala Phe Glu Ile Tyr Asn Lys Asp Leu Leu Ala Thr Glu
                595                 600                 605 aag aaa tac aca cac tat aat acg gca ctt tct tat gcc ctg ctt tta        1874
Lys Lys Tyr Thr His Tyr Asn Thr Ala Leu Ser Tyr Ala Leu Leu Leu
            610                 615                 620 acc aac aaa tcc agt gtg ccg cgt gtc tat tat ggg gat atg ttt aca        1922
Thr Asn Lys Ser Ser Val Pro Arg Val Tyr Tyr Gly Asp Met Phe Thr
            625                 630                 635 gat gac ggg caa tac atg gct cat aag acg atc aat tac gaa gcc atc        1970
Asp Asp Gly Gln Tyr Met Ala His Lys Thr Ile Asn Tyr Glu Ala Ile
640                 645                 650 gaa acc ctg ctt aaa gct cgt att aag tat gtt tca ggc ggt caa gcc        2018
Glu Thr Leu Leu Lys Ala Arg Ile Lys Tyr Val Ser Gly Gly Gln Ala
655                 660                 665                 670 atg cgc aat caa cag gtt ggc aat tct gaa atc att acg tct gtc cgc        2066
Met Arg Asn Gln Gln Val Gly Asn Ser Glu Ile Ile Thr Ser Val Arg
                675                 680                 685 tat ggt aaa ggt gct ttg aaa gca acg gat aca ggg gac cgc acc aca        2114
Tyr Gly Lys Gly Ala Leu Lys Ala Thr Asp Thr Gly Asp Arg Thr Thr
            690                 695                 700 cgg act tca gga gtg gcc gtg att gaa ggc aat aac cct tct tta cgt        2162
Arg Thr Ser Gly Val Ala Val Ile Glu Gly Asn Asn Pro Ser Leu Arg
            705                 710                 715 ttg aag gct tct gat cgc gtg gtt gtc aat atg gga gca gcc cat aag        2210
Leu Lys Ala Ser Asp Arg Val Val Val Asn Met Gly Ala Ala His Lys
            720                 725                 730 aac caa gct tac cga cct tta ctc ttg acc aca gat aac ggt atc aag        2258
Asn Gln Ala Tyr Arg Pro Leu Leu Leu Thr Thr Asp Asn Gly Ile Lys
735                 740                 745                 750 gct tat cat tcc gat caa gaa gcg gct ggt ttg gtg cgc tac acc aat        2306
Ala Tyr His Ser Asp Gln Glu Ala Ala Gly Leu Val Arg Tyr Thr Asn
                755                 760                 765 gac aga ggg gaa ttg atc ttc aca gcg gct gat att aaa ggc tat gcc        2354
Asp Arg Gly Glu Leu Ile Phe Thr Ala Ala Asp Ile Lys Gly Tyr Ala
            770                 775                 780 aac cct caa gtt tct ggc tat tta ggt gtc tgg gtt cca gta ggc gct        2402
Asn Pro Gln Val Ser Gly Tyr Leu Gly Val Trp Val Pro Val Gly Ala
            785                 790                 795 gcg ctg atc aag atg ttc gcg ttg cgg cta gca cgg ccc cat caa cag        2450
Ala Leu Ile Lys Met Phe Ala Leu Arg Leu Ala Arg Pro His Gln Gln
            800                 805                 810 atg gca agt gtg cat caa aat gcg gcc ctt gat tca cgc gtc atg ttt        2498
Met Ala Ser Val His Gln Asn Ala Ala Leu Asp Ser Arg Val Met Phe
815                 820                 825                 830
```

-continued

```
gaa ggt ttc tct aat ttc caa gct ttc gcc act aaa aaa gag gaa tat      2546
Glu Gly Phe Ser Asn Phe Gln Ala Phe Ala Thr Lys Lys Glu Glu Tyr
             835                 840                 845 acc aat gtt gtg att gct aag aat gtg gat aag ttt gcg gaa tgg ggg      2594
Thr Asn Val Val Ile Ala Lys Asn Val Asp Lys Phe Ala Glu Trp Gly
    850                 855                 860 gtc aca gac ttt gaa atg gca ccg cag tat gtg tct tca acg gat ggt      2642
Val Thr Asp Phe Glu Met Ala Pro Gln Tyr Val Ser Ser Thr Asp Gly
        865                 870                 875 tct ttc ttg gat tct gtg atc caa aac ggc tat gct ttt acg gac cgt      2690
Ser Phe Leu Asp Ser Val Ile Gln Asn Gly Tyr Ala Phe Thr Asp Arg
            880                 885                 890 tat gat ttg gga att tcc aaa cct aat aaa tac ggg aca gcc gat gat      2738
Tyr Asp Leu Gly Ile Ser Lys Pro Asn Lys Tyr Gly Thr Ala Asp Asp
895                 900                 905                 910 ttg gtg aaa gcc atc aaa gcg tta cac agc aag ggc att aag gta atg      2786
Leu Val Lys Ala Ile Lys Ala Leu His Ser Lys Gly Ile Lys Val Met
                915                 920                 925 gct gac tgg gtg cct gat caa atg tat gct ttc cct gaa aaa gaa gtg      2834
Ala Asp Trp Val Pro Asp Gln Met Tyr Ala Phe Pro Glu Lys Glu Val
            930                 935                 940 gta act gca acc cgt gtt gat aag tat ggg act cct gtt gca gga agt      2882
Val Thr Ala Thr Arg Val Asp Lys Tyr Gly Thr Pro Val Ala Gly Ser
945                 950                 955 cag atc aaa aac acc ctt tat gta gtt gat ggt aag agt tct ggt aaa      2930
Gln Ile Lys Asn Thr Leu Tyr Val Val Asp Gly Lys Ser Ser Gly Lys
    960                 965                 970 gat caa caa gcc aag tat ggg gga gct ttc tta gag gag ctg caa gcg      2978
Asp Gln Gln Ala Lys Tyr Gly Gly Ala Phe Leu Glu Glu Leu Gln Ala
975                 980                 985                 990 aag tat ccg gag ctt ttt gcg aga aaa caa att tcc aca ggg gtt ccg      3026
Lys Tyr Pro Glu Leu Phe Ala Arg Lys Gln Ile Ser Thr Gly Val Pro
                995                1000                1005 atg gat cct tct gtt aag att aag caa tgg tct gcc aag tac ttt aat      3074
Met Asp Pro Ser Val Lys Ile Lys Gln Trp Ser Ala Lys Tyr Phe Asn
            1010                1015                1020 ggg aca aat att tta ggg cgc gga gca ggc tat gtc tta aaa gat cag      3122
Gly Thr Asn Ile Leu Gly Arg Gly Ala Gly Tyr Val Leu Lys Asp Gln
        1025                1030                1035 gca act aat act tac ttt aat att tca gat aat aaa gaa ata aac ttc      3170
Ala Thr Asn Thr Tyr Phe Asn Ile Ser Asp Asn Lys Glu Ile Asn Phe
    1040                1045                1050 ctt cct aaa aca ttg tta aac caa gat agt caa gtt ggt ttc tct tat      3218
Leu Pro Lys Thr Leu Leu Asn Gln Asp Ser Gln Val Gly Phe Ser Tyr
1055                1060                1065                1070 gac ggt aaa ggt tat gtt tat tat tca acg agt ggt tac caa gcc aaa      3266
Asp Gly Lys Gly Tyr Val Tyr Tyr Ser Thr Ser Gly Tyr Gln Ala Lys
                1075                1080                1085 aat act ttc atc agc gaa ggt gat aaa tgg tat tat ttt gat aat aac      3314
Asn Thr Phe Ile Ser Glu Gly Asp Lys Trp Tyr Tyr Phe Asp Asn Asn
            1090                1095                1100 ggt tat atg gtc act ggt gct caa tca att aac ggt gtt aat tat tat      3362
Gly Tyr Met Val Thr Gly Ala Gln Ser Ile Asn Gly Val Asn Tyr Tyr
        1105                1110                1115 ttc tta tca aat ggc cta cag ctc aga gat gct att ctt aag aat gaa      3410
Phe Leu Ser Asn Gly Leu Gln Leu Arg Asp Ala Ile Leu Lys Asn Glu
    1120                1125                1130 gat gga act tac gct tat tat gga aat gac ggt cgc cgt tat gaa aat      3458
Asp Gly Thr Tyr Ala Tyr Tyr Gly Asn Asp Gly Arg Arg Tyr Glu Asn
1135                1140                1145                1150
```

```
ggt tat tat caa ttc atg agt ggt gta tgg cgt cac ttc aat aat ggt      3506
Gly Tyr Tyr Gln Phe Met Ser Gly Val Trp Arg His Phe Asn Asn Gly
                1155                1160                1165 gaa atg agt gtt gga tta act gta att gat ggt cag gtt caa tac ttt      3554
Glu Met Ser Val Gly Leu Thr Val Ile Asp Gly Gln Val Gln Tyr Phe
                1170                1175                1180 gat gaa atg ggc tat caa gcc aaa gga aaa ttt gta aca act gcc gat      3602
Asp Glu Met Gly Tyr Gln Ala Lys Gly Lys Phe Val Thr Thr Ala Asp
                1185                1190                1195 ggt aaa ata aga tat ttt gat aag caa tct ggg aac atg tac cgt aat      3650
Gly Lys Ile Arg Tyr Phe Asp Lys Gln Ser Gly Asn Met Tyr Arg Asn
                1200                1205                1210 cgt ttt att gaa aac gaa gaa ggt aaa tgg ctg tat ctc ggt gaa gat      3698
Arg Phe Ile Glu Asn Glu Glu Gly Lys Trp Leu Tyr Leu Gly Glu Asp
1215                1220                1225                1230 ggt gca gca gtg aca gga tct caa acc att aac ggt caa cac ctg tac      3746
Gly Ala Ala Val Thr Gly Ser Gln Thr Ile Asn Gly Gln His Leu Tyr
                1235                1240                1245 ttt aga gca aac ggt gtt cag gtc aag ggt gaa ttt gtc act gac cac      3794
Phe Arg Ala Asn Gly Val Gln Val Lys Gly Glu Phe Val Thr Asp His
                1250                1255                1260 cac ggc cgt atc agc tat tac gac ggc aat tca ggg gat caa atc cgc      3842
His Gly Arg Ile Ser Tyr Tyr Asp Gly Asn Ser Gly Asp Gln Ile Arg
                1265                1270                1275 aac cgc ttt gtc cgc aat gct cag ggt caa tgg ttc tac ttt gat aac      3890
Asn Arg Phe Val Arg Asn Ala Gln Gly Gln Trp Phe Tyr Phe Asp Asn
                1280                1285                1290 aat ggc tat gcc gta acc ggt gcc aga acc att aac ggt caa ctc cta      3938
Asn Gly Tyr Ala Val Thr Gly Ala Arg Thr Ile Asn Gly Gln Leu Leu
1295                1300                1305                1310 tac ttt aga gca aac ggt gtt cag gtc aag ggt gaa ttt gtc act gac      3986
Tyr Phe Arg Ala Asn Gly Val Gln Val Lys Gly Glu Phe Val Thr Asp
                1315                1320                1325 cgc tac ggc cgt atc agc tat tac gac ggc aat tca ggg gat caa atc      4034
Arg Tyr Gly Arg Ile Ser Tyr Tyr Asp Gly Asn Ser Gly Asp Gln Ile
                1330                1335                1340 cgc aac cgc ttt gtc cgc aat gct cag ggt caa tgg ttc tac ttt gat      4082
Arg Asn Arg Phe Val Arg Asn Ala Gln Gly Gln Trp Phe Tyr Phe Asp
                1345                1350                1355 aac aat ggc tat gcc gta acc ggt gcc aga acc att aac ggt caa cac      4130
Asn Asn Gly Tyr Ala Val Thr Gly Ala Arg Thr Ile Asn Gly Gln His
                1360                1365                1370 cta tac ttt aga gca aac ggt gtt cag gtc aag ggt gaa ttt gtc act      4178
Leu Tyr Phe Arg Ala Asn Gly Val Gln Val Lys Gly Glu Phe Val Thr
1375                1380                1385                1390 gac cgc cac ggc cgt atc agc tat tac gac ggc aat tca ggg gat caa      4226
Asp Arg His Gly Arg Ile Ser Tyr Tyr Asp Gly Asn Ser Gly Asp Gln
                1395                1400                1405 atc cgc aac cgc ttt gtc cgc aat gct cag ggt caa tgg ttc tac ttt      4274
Ile Arg Asn Arg Phe Val Arg Asn Ala Gln Gly Gln Trp Phe Tyr Phe
                1410                1415                1420 gat aac aat ggc tat gcc gta acc ggt gcc aga acc att aac ggt caa      4322
Asp Asn Asn Gly Tyr Ala Val Thr Gly Ala Arg Thr Ile Asn Gly Gln
                1425                1430                1435 cac cta tac ttt aga gca aac ggt gtt cag gtc aag ggt gaa ttt gtc      4370
His Leu Tyr Phe Arg Ala Asn Gly Val Gln Val Lys Gly Glu Phe Val
                1440                1445                1450 act gac cgc tac ggc cgt atc agt tat tac gat gct aac tct gga gaa      4418
Thr Asp Arg Tyr Gly Arg Ile Ser Tyr Tyr Asp Ala Asn Ser Gly Glu
```

```
                  1455          1460          1465          1470
cga gtt cgg att aac t aattgttttt tcgctctctt aagtta                    4460
Arg Val Arg Ile Asn
                1475
```

<210> SEQ ID NO 2
<211> LENGTH: 1475
<212> TYPE: PRT
<213> ORGANISM: Streptococcus mutans

<400> SEQUENCE: 2

```
Met Asp Lys Lys Val Arg Tyr Lys Leu Arg Lys Val Lys Arg Trp
 1               5                  10                  15

Val Thr Val Ser Val Ala Ser Ala Val Met Thr Leu Thr Thr Leu Ser
                20                  25                  30

Gly Gly Leu Val Lys Ala Asp Ser Asn Glu Ser Lys Ser Gln Ile Ser
                35                  40                  45

Asn Asp Ser Asn Thr Ser Val Val Thr Ala Asn Glu Glu Ser Asn Val
50                  55                  60

Ile Thr Glu Ala Thr Ser Lys Gln Glu Ala Ala Ser Ser Gln Thr Asn
65                  70                  75                  80

His Thr Val Thr Thr Ser Ser Ser Ser Thr Ser Val Val Asn Pro Lys
                85                  90                  95

Glu Val Val Ser Asn Pro Tyr Thr Val Gly Glu Thr Ala Ser Asn Gly
                100                 105                 110

Glu Lys Leu Gln Asn Gln Thr Thr Val Asp Lys Thr Ser Glu Ala
                115                 120                 125

Ala Ala Asn Asn Ile Ser Lys Gln Thr Thr Glu Ala Asp Thr Asp Val
130                 135                 140

Ile Asp Ser Asn Ala Ala Asn Leu Gln Ile Leu Glu Lys Leu Pro
145                 150                 155                 160

Asn Val Lys Glu Ile Asp Gly Lys Tyr Tyr Tyr Asp Asn Asn Gly
                165                 170                 175

Lys Val Arg Thr Asn Phe Thr Leu Ile Ala Asp Gly Lys Ile Leu His
                180                 185                 190

Phe Asp Glu Thr Gly Ala Tyr Thr Asp Thr Ser Ile Asp Thr Val Asn
                195                 200                 205

Lys Asp Ile Val Thr Thr Arg Ser Asn Leu Tyr Lys Lys Tyr Asn Gln
                210                 215                 220

Val Tyr Asp Arg Ser Ala Gln Ser Phe Glu His Val Asp His Tyr Leu
225                 230                 235                 240

Thr Ala Glu Ser Trp Tyr Arg Pro Lys Tyr Ile Leu Lys Asp Gly Lys
                245                 250                 255

Thr Trp Thr Gln Ser Thr Glu Lys Asp Phe Arg Pro Leu Leu Met Thr
                260                 265                 270

Trp Trp Pro Asp Gln Glu Thr Gln Arg Gln Tyr Val Asn Tyr Met Asn
                275                 280                 285

Ala Gln Leu Gly Ile Asn Lys Thr Tyr Asp Asp Thr Ser Asn Gln Leu
                290                 295                 300

Gln Leu Asn Ile Ala Ala Ala Thr Ile Gln Ala Lys Ile Glu Ala Lys
305                 310                 315                 320

Ile Thr Thr Leu Lys Asn Thr Asp Trp Leu Arg Gln Thr Ile Ser Ala
                325                 330                 335

Phe Val Lys Thr Gln Ser Ala Trp Asn Ser Asp Ser Glu Lys Pro Phe
                340                 345                 350
```

```
Asp Asp His Leu Gln Asn Gly Ala Val Leu Tyr Asp Asn Glu Gly Lys
        355                 360                 365

Leu Thr Pro Tyr Ala Asn Ser Asn Tyr Arg Ile Leu Asn Arg Thr Pro
370                 375                 380

Thr Asn Gln Thr Gly Lys Lys Asp Pro Arg Tyr Thr Ala Asp Asn Thr
385                 390                 395                 400

Ile Gly Gly Tyr Glu Phe Leu Leu Ala Asn Asp Val Asp Asn Ser Asn
                405                 410                 415

Pro Val Val Gln Ala Glu Gln Leu Asn Trp Leu His Phe Leu Met Asn
            420                 425                 430

Phe Gly Asn Ile Tyr Ala Asn Asp Pro Asp Ala Asn Phe Asp Ser Ile
        435                 440                 445

Arg Val Asp Ala Val Asp Asn Val Asp Ala Asp Leu Leu Gln Ile Ala
    450                 455                 460

Gly Asp Tyr Leu Lys Ala Lys Gly Ile His Lys Asn Asp Lys Ala
465                 470                 475                 480

Ala Asn Asp His Leu Ser Ile Leu Glu Ala Trp Ser Asp Asn Asp Thr
                485                 490                 495

Pro Tyr Leu His Asp Asp Gly Asp Asn Met Ile Asn Met Asp Asn Lys
            500                 505                 510

Leu Arg Leu Ser Leu Leu Phe Ser Leu Ala Lys Pro Leu Asn Gln Arg
        515                 520                 525

Ser Gly Met Asn Pro Leu Ile Thr Asn Ser Leu Val Asn Arg Thr Asp
    530                 535                 540

Asp Asn Ala Glu Thr Ala Ala Val Pro Ser Tyr Ser Phe Ile Arg Ala
545                 550                 555                 560

His Asp Ser Glu Val Gln Asp Leu Ile Ala Asp Ile Ile Lys Ala Glu
                565                 570                 575

Ile Asn Pro Asn Val Val Gly Tyr Ser Phe Thr Met Glu Glu Ile Lys
            580                 585                 590

Lys Ala Phe Glu Ile Tyr Asn Lys Asp Leu Leu Ala Thr Glu Lys Lys
        595                 600                 605

Tyr Thr His Tyr Asn Thr Ala Leu Ser Tyr Ala Leu Leu Leu Thr Asn
    610                 615                 620

Lys Ser Ser Val Pro Arg Val Tyr Tyr Gly Asp Met Phe Thr Asp Asp
625                 630                 635                 640

Gly Gln Tyr Met Ala His Lys Thr Ile Asn Tyr Glu Ala Ile Glu Thr
                645                 650                 655

Leu Leu Lys Ala Arg Ile Lys Tyr Val Ser Gly Gln Ala Met Arg
        660                 665                 670

Asn Gln Gln Val Gly Asn Ser Glu Ile Ile Thr Ser Val Arg Tyr Gly
            675                 680                 685

Lys Gly Ala Leu Lys Ala Thr Asp Thr Gly Asp Arg Thr Thr Arg Thr
        690                 695                 700

Ser Gly Val Ala Val Ile Glu Gly Asn Asn Pro Ser Leu Arg Leu Lys
705                 710                 715                 720

Ala Ser Asp Arg Val Val Asn Met Gly Ala Ala His Lys Asn Gln
                725                 730                 735

Ala Tyr Arg Pro Leu Leu Leu Thr Thr Asp Asn Gly Ile Lys Ala Tyr
            740                 745                 750

His Ser Asp Gln Glu Ala Ala Gly Leu Val Arg Tyr Thr Asn Asp Arg
        755                 760                 765
```

-continued

```
Gly Glu Leu Ile Phe Thr Ala Ala Asp Ile Lys Gly Tyr Ala Asn Pro
    770                 775                 780

Gln Val Ser Gly Tyr Leu Gly Val Trp Val Pro Val Gly Ala Ala Leu
785                 790                 795                 800

Ile Lys Met Phe Ala Leu Arg Leu Ala Arg Pro His Gln Gln Met Ala
                805                 810                 815

Ser Val His Gln Asn Ala Ala Leu Asp Ser Arg Val Met Phe Glu Gly
            820                 825                 830

Phe Ser Asn Phe Gln Ala Phe Ala Thr Lys Lys Glu Glu Tyr Thr Asn
        835                 840                 845

Val Val Ile Ala Lys Asn Val Asp Lys Phe Ala Glu Trp Gly Val Thr
    850                 855                 860

Asp Phe Glu Met Ala Pro Gln Tyr Val Ser Ser Thr Asp Gly Ser Phe
865                 870                 875                 880

Leu Asp Ser Val Ile Gln Asn Gly Tyr Ala Phe Thr Asp Arg Tyr Asp
                885                 890                 895

Leu Gly Ile Ser Lys Pro Asn Lys Tyr Gly Thr Ala Asp Asp Leu Val
            900                 905                 910

Lys Ala Ile Lys Ala Leu His Ser Lys Gly Ile Lys Val Met Ala Asp
        915                 920                 925

Trp Val Pro Asp Gln Met Tyr Ala Phe Pro Gly Lys Glu Val Val Thr
    930                 935                 940

Ala Thr Arg Val Asp Lys Tyr Gly Thr Pro Val Ala Gly Ser Gln Ile
945                 950                 955                 960

Lys Asn Thr Leu Tyr Val Val Asp Gly Lys Ser Ser Gly Lys Asp Gln
                965                 970                 975

Gln Ala Lys Tyr Gly Gly Ala Phe Leu Glu Glu Leu Gln Ala Lys Tyr
            980                 985                 990

Pro Glu Leu Phe Ala Arg Lys Gln Ile Ser Thr Gly Val Pro Met Asp
        995                 1000                1005

Pro Ser Val Lys Ile Lys Gln Trp Ser Ala Lys Tyr Phe Asn Gly Thr
    1010                1015                1020

Asn Ile Leu Gly Arg Gly Ala Gly Tyr Val Leu Lys Asp Gln Ala Thr
1025                1030                1035                1040

Asn Thr Tyr Phe Asn Ile Ser Asp Asn Lys Glu Ile Asn Phe Leu Pro
                1045                1050                1055

Lys Thr Leu Leu Asn Gln Asp Ser Gln Val Gly Phe Ser Tyr Asp Gly
            1060                1065                1070

Lys Gly Tyr Val Tyr Tyr Ser Thr Ser Gly Tyr Gln Ala Lys Asn Thr
        1075                1080                1085

Phe Ile Ser Glu Gly Asp Lys Trp Tyr Tyr Phe Asp Asn Asn Gly Tyr
    1090                1095                1100

Met Val Thr Gly Ala Gln Ser Ile Asn Gly Val Asn Tyr Tyr Phe Leu
1105                1110                1115                1120

Ser Asn Gly Leu Gln Leu Arg Asp Ala Ile Leu Lys Asn Glu Asp Gly
                1125                1130                1135

Thr Tyr Ala Tyr Tyr Gly Asn Asp Gly Arg Arg Tyr Glu Asn Gly Tyr
            1140                1145                1150

Tyr Gln Phe Met Ser Gly Val Trp Arg His Phe Asn Asn Gly Glu Met
        1155                1160                1165

Ser Val Gly Leu Thr Val Ile Asp Gly Gln Val Gln Tyr Phe Asp Glu
    1170                1175                1180

Met Gly Tyr Gln Ala Lys Gly Lys Phe Val Thr Thr Ala Asp Gly Lys
```

```
                                -continued
1185                  1190                1195                      1200

Ile Arg Tyr Phe Asp Lys Gln Ser Gly Asn Met Tyr Arg Asn Arg Phe
                    1205                1210                1215

Ile Glu Asn Glu Glu Gly Lys Trp Leu Tyr Leu Gly Glu Asp Gly Ala
                1220                1225                1230

Ala Val Thr Gly Ser Gln Thr Ile Asn Gly Gln His Leu Tyr Phe Arg
            1235                1240                1245

Ala Asn Gly Val Gln Val Lys Gly Glu Phe Val Thr Asp His His Gly
        1250                1255                1260

Arg Ile Ser Tyr Tyr Asp Gly Asn Ser Gly Asp Gln Ile Arg Asn Arg
1265                1270                1275                1280

Phe Val Arg Asn Ala Gln Gly Gln Trp Phe Tyr Phe Asp Asn Asn Gly
                1285                1290                1295

Tyr Ala Val Thr Gly Ala Arg Thr Ile Asn Gly Gln Leu Leu Tyr Phe
            1300                1305                1310

Arg Ala Asn Gly Val Gln Val Lys Gly Glu Phe Val Thr Asp Arg Tyr
        1315                1320                1325

Gly Arg Ile Ser Tyr Tyr Asp Gly Asn Ser Gly Asp Gln Ile Arg Asn
            1330                1335                1340

Arg Phe Val Arg Asn Ala Gln Gly Gln Trp Phe Tyr Phe Asp Asn Asn
1345                1350                1355                1360

Gly Tyr Ala Val Thr Gly Ala Arg Thr Ile Asn Gly Gln His Leu Tyr
                1365                1370                1375

Phe Arg Ala Asn Gly Val Gln Val Lys Gly Glu Phe Val Thr Asp Arg
            1380                1385                1390

His Gly Arg Ile Ser Tyr Tyr Asp Gly Asn Ser Gly Asp Gln Ile Arg
        1395                1400                1405

Asn Arg Phe Val Arg Asn Ala Gln Gly Gln Trp Phe Tyr Phe Asp Asn
    1410                1415                1420

Asn Gly Tyr Ala Val Thr Gly Ala Arg Thr Ile Asn Gly Gln His Leu
1425                1430                1435                1440

Tyr Phe Arg Ala Asn Gly Val Gln Val Lys Gly Glu Phe Val Thr Asp
                1445                1450                1455

Arg Tyr Gly Arg Ile Ser Tyr Tyr Asp Ala Asn Ser Gly Glu Arg Val
            1460                1465                1470

Arg Ile Asn
        1475
```